(12) United States Patent
Kataoka et al.

(10) Patent No.: US 11,832,981 B2
(45) Date of Patent: Dec. 5, 2023

(54) X-RAY FLUORESCENCE SPECTROMETER

(71) Applicant: Rigaku Corporation, Tokyo (JP)

(72) Inventors: Yoshiyuki Kataoka, Otsu (JP); Yasuhiko Nagoshi, Kobe (JP); Eiichi Furusawa, Ibaraki (JP)

(73) Assignee: Rigaku Corporation, Akishima (JP)

( * ) Notice: Subject to any disclaimer, the term of this patent is extended or adjusted under 35 U.S.C. 154(b) by 0 days.

(21) Appl. No.: 18/202,499

(22) Filed: May 26, 2023

(65) Prior Publication Data
US 2023/0293129 A1 Sep. 21, 2023

Related U.S. Application Data

(63) Continuation of application No. PCT/JP2021/033636, filed on Sep. 14, 2021.

(30) Foreign Application Priority Data

Nov. 30, 2020 (JP) .................. 2020-198816

(51) Int. Cl.
*G01N 23/223* (2006.01)
*A61B 6/00* (2006.01)

(52) U.S. Cl.
CPC .................. *A61B 6/48* (2013.01); *A61B 6/54* (2013.01); *G01N 23/223* (2013.01)

(58) Field of Classification Search
CPC ........... G01N 23/223; G01N 2223/076; G01N 23/2076; G01N 2223/633; G01N 2223/1016; G01N 35/00; G01N 23/22; G01N 23/2208; G01N 21/3563; G01B 15/02
See application file for complete search history.

(56) References Cited

U.S. PATENT DOCUMENTS 6,081,579 A    6/2000  Nagano et al.
7,362,844 B2   4/2008  Heismann et al.
(Continued)

FOREIGN PATENT DOCUMENTS

JP    61-175555 A    8/1986
JP    02-226058 A    9/1990
(Continued)

OTHER PUBLICATIONS

Dr. Hisayuki Kohno (Sci.), X-Ray Fluorescence Spectroscopy Introduction and Applications, , Rigaku Corporation, Dec. 2011, pp. 62 and 165-166, First Edition.
(Continued)

*Primary Examiner* — Don K Wong
(74) *Attorney, Agent, or Firm* — Sughrue Mion, PLLC

(57) ABSTRACT

By regarding total precision of an X-ray intensity as counting precision due to statistical fluctuation and counting loss and by regarding the counting precision as a product of precision of an uncorrected intensity, which is an intensity before counting loss correction is performed, and a gradient of a corrected intensity with respect to the uncorrected intensity, a counting time calculation unit (13) included in an X-ray fluorescence spectrometer of the present invention calculates a counting time from specified total precision of the X-ray intensity, a given counting loss correction coefficient, and a given corrected intensity for each measurement line (5).

4 Claims, 2 Drawing Sheets

(56) References Cited

U.S. PATENT DOCUMENTS

| | | |
|---|---|---|
| 8,774,356 B2 | 7/2014 | Kataoka et al. |
| 8,901,493 B2 | 12/2014 | Kaji |
| 2006/0034418 A1 | 2/2006 | Heismann et al. |
| 2012/0241611 A1 | 9/2012 | Kaji |
| 2013/0294577 A1 | 11/2013 | Kataoka et al. |

FOREIGN PATENT DOCUMENTS

| | | | |
|---|---|---|---|
| JP | 9-297112 A | | 11/1997 |
| JP | 2000-065765 A | | 3/2000 |
| JP | 2000-074857 A | | 3/2000 |
| JP | 2001-21511 A | | 1/2001 |
| JP | 2002082075 A | * | 3/2002 |
| JP | 2006-58296 A | | 3/2006 |
| JP | 2006-118941 A | | 5/2006 |
| JP | 2008-191044 A | | 8/2008 |
| JP | 2012-242285 A | | 12/2012 |
| JP | 2019-090652 A | | 6/2019 |
| WO | 2011/070704 A1 | | 6/2011 |

OTHER PUBLICATIONS

International Search Report for PCT/JP2021/033636 dated Nov. 30, 2021.
Written Opinion for PCT/JP2021/033636 dated Nov. 30, 2021.
Decision to Grant a Patent dated Nov. 1, 2022 in corresponding Japanese Patent Application No. 2020-198816, 6 pages.
International Preliminary Report on Patentability dated Jun. 15, 2023 in International Application No. PCT/JP2021/033636.

* cited by examiner

X-RAY FLUORESCENCE SPECTROMETER

CROSS REFERENCE TO THE RELATED APPLICATION

This application is a continuation application, under 35 U.S.C. § 111(a), of international application No. PCT/JP2021/033636, filed Sep. 14, 2021, which claims priority to Japanese patent application No. 2020-198816, filed Nov. 30, 2020, the entire disclosures of all of which are herein incorporated by reference as a part of this application.

BACKGROUND OF THE INVENTION

Field of the Invention

The present invention relates to an X-ray fluorescence spectrometer which performs quantitative analysis of various samples, based on corrected intensities obtained by irradiating a sample with primary X-rays, measuring intensities of generated secondary X-rays, and performing counting loss correction.

Description of Related Art

In quantitative analysis by an X-ray fluorescence spectrometer, an X-ray intensity is counted for each of analytical elements corresponding to analytical components, and quantitative calculation is performed from the obtained X-ray intensity, for example, by a calibration curve method. The precision of the X-ray intensity for each component, that is, the counting precision for each component, depends on the X-ray intensity and the counting time. As for the counting precision, usually, when the counted value of X-ray intensity is expressed by an integrated intensity (count number c), the precision of the integrated intensity is expressed by the square root of the integrated intensity. This phenomenon is called statistical fluctuation. When the counting precision is due to statistical fluctuation as described above, if the unit of an X-ray intensity I is cps and the unit of a counting time T is seconds, the counting precision $\sigma_{Count}$ (cps) can be calculated by the following equation (1).

$$\sigma_{Count} = (I/T)^{1/2} \qquad (1)$$

Moreover, by transforming equation (1), a counting time T at which specified counting precision $\sigma_{Count}$ is obtained can be calculated as in the following equation (2).

$$T = I/\sigma_{Count}^2 \qquad (2)$$

There is a spectrometer that, using this, in order to perform measurement with an appropriate counting time and appropriate analysis precision, on the assumption that relative precision of counting and relative precision of an analytical value (relative precision of a concentration) coincide with each other, calculates a counting time such that the relative precision of counting, that is, the relative precision of the analytical value, becomes a specified value (see, for example, Patent Document 1).

Moreover, there is also a spectrometer that uses total precision of an X-ray intensity as the precision of the X-ray intensity and regards a square of the total precision of the X-ray intensity as a sum of a square of counting precision due to statistical fluctuation and a square of hardware reproducibility precision due to hardware reproducibility of the spectrometer (see, for example, Patent Document 2).

In these conventional spectrometers, counting loss correction is performed as necessary for the measured intensity of secondary X-rays such as fluorescent X-rays (see, for example, Non-Patent Document 1), the corrected intensity is considered to correspond to the true X-ray intensity incident on a detector, and quantitative analysis is performed based on the corrected intensity. Therefore, the corrected intensity is also used as the X-ray intensity I in the previous equation (1), and the counting precision $\sigma_{Count}$ is obtained.

RELATED DOCUMENT

Patent Document

[Patent Document 1] JP Laid-open Patent Publication No. 2000-074857
[Patent Document 2] JP Laid-open Patent Publication No. 2019-090652

Non-Patent Document

[Non-Patent Document 1] Hisayuki Kohno, "Keikou Ekkususen Bunseki Kiso To Ouyou (X-Ray Fluorescence Spectroscopy Introduction and Applications)", first edition, Rigaku Corporation, December 2011, p. 62, p. 165-166

SUMMARY OF THE INVENTION

However, in reality, as the true X-ray intensity incident on the detector increases, counting loss occurs more frequently, and the deviation between the uncorrected intensity and the true X-ray intensity increases even if the corrected intensity is substantially equal to the true X-ray intensity. Thus, when counting loss occurs, even if the corrected intensity is used as the X-ray intensity I in the previous equation (1), the counting precision $\sigma_{Count}$ cannot be obtained correctly, and eventually the total precision of the X-ray intensity cannot be obtained correctly. Therefore, with the conventional spectrometer, it is not possible to perform measurement with an appropriate counting time and appropriate analysis precision when counting loss occurs.

The present invention has been made in view of the problems of the conventional art, and an object of the present invention is to provide an X-ray fluorescence spectrometer capable of performing measurement with an appropriate counting time and appropriate analysis precision even when counting loss occurs.

In order to achieve the above-described object, a first aspect of the present invention is directed to an X-ray fluorescence spectrometer which obtains a quantitative value of a content of a component in a sample and/or a quantitative value of a thickness of the sample, based on corrected intensities obtained by irradiating the sample with primary X-rays, measuring intensities of generated secondary X-rays, and performing counting loss correction, the X-ray fluorescence spectrometer including a counting time calculation unit configured to calculate a counting time for each of measurement lines which are secondary X-rays to be measured for intensities.

By regarding total precision of an X-ray intensity as counting precision due to statistical fluctuation and counting loss, and by regarding the counting precision as a product of precision of an uncorrected intensity, which is an intensity before the counting loss correction is performed, and a gradient of the corrected intensity with respect to the uncorrected intensity, the counting time calculation unit calculates the counting time from specified total precision of the X-ray intensity, a given counting loss correction coefficient, and a given corrected intensity for each measurement line.

In the X-ray fluorescence spectrometer according to the first aspect, by regarding the counting precision as the product of the precision of the uncorrected intensity, which is the intensity before the counting loss correction is performed, and the gradient of the corrected intensity with respect to the uncorrected intensity, the effect of counting loss is appropriately reflected in the counting precision. Thus, even when counting loss occurs, the counting time can be calculated correctly from the specified total precision of the X-ray intensity, and measurement can be performed with an appropriate counting time and appropriate analysis precision.

A second aspect of the present invention is directed to an X-ray fluorescence spectrometer which obtains a quantitative value of a content of a component in a sample and/or a quantitative value of a thickness of the sample, based on corrected intensities obtained by irradiating the sample with primary X-rays, measuring intensities of generated secondary X-rays, and performing counting loss correction, the X-ray fluorescence spectrometer including a total precision calculation unit configured to calculate total precision of an X-ray intensity for each of measurement lines which are secondary X-rays to be measured for intensities.

By regarding the total precision of the X-ray intensity as counting precision due to statistical fluctuation and counting loss, and by regarding the counting precision as a product of precision of an uncorrected intensity, which is an intensity before the counting loss correction is performed, and a gradient of the corrected intensity with respect to the uncorrected intensity, the total precision calculation unit calculates the total precision of the X-ray intensity from a specified counting time, a given counting loss correction coefficient, and a given corrected intensity for each measurement line.

In the X-ray fluorescence spectrometer according to the second aspect as well, by regarding the counting precision as the product of the precision of the uncorrected intensity, which is the intensity before the counting loss correction is performed, and the gradient of the corrected intensity with respect to the uncorrected intensity, the effect of counting loss is appropriately reflected in the counting precision. Thus, even when counting loss occurs, the total precision of the X-ray intensity can be calculated correctly from the specified counting time, and measurement can be performed with an appropriate counting time and appropriate analysis precision.

In the X-ray fluorescence spectrometers according to the first aspect and the second aspect, hardware reproducibility precision due to hardware reproducibility of the X-ray fluorescence spectrometer may be taken into consideration for the total precision of the X-ray intensity. In this case, instead of regarding the total precision of the X-ray intensity as the counting precision due to statistical fluctuation and counting loss, a square of the total precision of the X-ray intensity is regarded as a sum of a square of the counting precision due to statistical fluctuation and counting loss and a square of the hardware reproducibility precision.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF THE EMBODIMENTS

Figure 1:
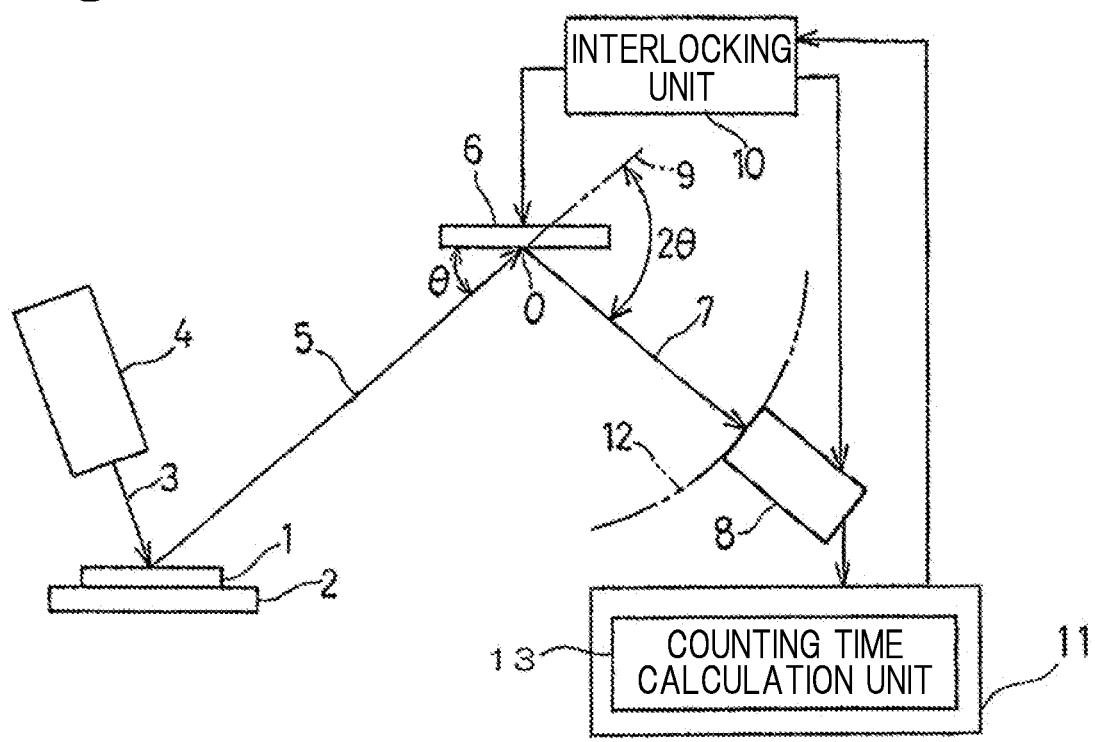
FIG. 1 is a schematic diagram showing an X-ray fluorescence spectrometer of a first embodiment of the present invention.

Hereinafter, a spectrometer of a first embodiment of the present invention will be described with reference to the drawing. As shown in FIG. 1, this spectrometer is an X-ray fluorescence spectrometer that, based on corrected intensities obtained by irradiating a sample 1 (including both an unknown sample and a standard sample) with primary X-rays 3, measuring intensities of generated secondary X-rays 5, and performing counting loss correction, obtains a quantitative value (an analytical value) of a content of a component in the sample 1 and/or a quantitative value of a thickness of the sample 1, and includes a sample stage 2 on which the sample 1 is placed, an X-ray source 4 such as an X-ray tube which irradiates the sample 1 with the primary X-rays 3, a spectroscopic device 6 which monochromates the secondary X-rays 5 such as fluorescent X-rays generated from the sample 1, and a detector 8 on which secondary X-rays 7 monochromated by the spectroscopic device 6 are incident and which detects an intensity of the secondary X-rays 7. An output of the detector 8 is input to a control unit 11 such as a computer which controls the entire spectrometer, via an amplifier, a pulse height analyzer, a counting unit, etc., which are not shown.

This spectrometer is a wavelength dispersive and sequential X-ray fluorescence spectrometer including an interlocking unit 10 (i.e. a so-called goniometer) configured to interlock the spectroscopic device 6 and the detector 8 so as to change the wavelength of the secondary X-rays 7 entering the detector 8. When the secondary X-rays 5 enter the spectroscopic device 6 at a certain incident angle $\theta$, an extension line 9 of the secondary X-rays 5 and the secondary X-rays 7 monochromated (diffracted) by the spectroscopic device 6 define a spectroscopic angle $2\theta$ therebetween, which corresponds to twice the incident angle $\theta$. The interlocking unit 10 is configured to rotate the spectroscopic device 6 by a rotation angle about an axis O, which passes through a center of a surface of the spectroscopic device 6 and which is perpendicular to the sheet of the drawing, and to rotate the detector 8 by an angle twice as wide as the rotation angle of the spectroscopic device 6 about the axis O along a circle 12, so that the spectroscopic angle $2\theta$ is changed so as to change the wavelengths of the secondary X-rays 7 to be monochromated while the monochromated secondary X-rays 7 is allowed to enter the detector 8. The value of the spectroscopic angle 2θ (angle of 2θ) is input into the control unit 11 from the interlocking unit 10.

For each of measurement lines that are the secondary X-rays 5 to be measured for intensity, the control unit 11 stops the interlocking unit 10 at the corresponding spectroscopic angle 2θ for a determined counting time and obtains a measured intensity. If necessary, the control unit 11 performs counting loss correction on the measured intensity and obtains a corrected intensity. The counting loss correction may be performed before input to the control unit 11. For each measurement line, a gross intensity obtained by measuring only a peak may be used as the measured intensity, or a net intensity obtained by measuring the peak and its background(s) and performing background subtraction may be used as the measured intensity. In addition, the quantitative calculation method for obtaining a quantitative value based on the measured intensities or the corrected intensities may be either a calibration curve method or a fundamental parameter method (hereinafter, also referred to as FP method).

The spectrometer of the first embodiment includes a counting time calculation unit 13 which calculates a counting time for each measurement line 5, as a program incorporated in the control unit 11. In the calculation by the counting time calculation unit 13, as in the following equation (3), a square of total precision $\sigma_{Total}$ of the X-ray intensity is regarded as a sum of a square of counting precision $\sigma_{Count}$ due to statistical fluctuation and counting loss and a square of hardware reproducibility precision $\sigma_{Inst}$ due to hardware reproducibility of the X-ray fluorescence spectrometer.

$$\sigma_{Total}^2 = \sigma_{Count}^2 + \sigma_{Inst}^2 \quad (3)$$

Here, the hardware reproducibility is reproducibility due to all fluctuation factors other than a variation due to the counting of the X-ray fluorescence spectrometer, and includes reproducibility due to mechanical factors, the reproducibility due to electrical factors, and reproducibility due to sample preparation. The reproducibility due to mechanical factors is reproducibility due to drive or replacement of mechanical elements, and includes, for example, angle reproducibility due to goniometer drive, position reproducibility due to replacement of the spectroscopic device, a slit, a primary X-ray filter, and a sample holder, etc. In addition, the reproducibility due to electrical factors is reproducibility due to fluctuations of a tube voltage, a tube current, etc., and the reproducibility due to sample preparation includes reproducibility due to pellet preparation with a powder press and reproducibility due to sample preparation with glass beads or the like. Since the hardware reproducibility precision $\sigma_{Inst}$ does not depend on the X-ray intensity, when each precision in equation (3) is divided by the average value of the X-ray intensity in all the measurement lines, the following equation (4) holds for total relative precision $\sigma_{RelTotal}$ of the X-ray intensity, counting relative precision $\sigma_{RelCount}$, and hardware reproducibility relative precision $\sigma_{RelInst}$.

$$\sigma_{RelTotal}^2 = \sigma_{RelCount}^2 + \sigma_{RelInst}^2 \quad (4)$$

By transforming equation (4), the hardware reproducibility relative precision σRelInst is expressed as the following equation (5).

$$\sigma_{RelInst} = (\sigma_{RelTotal}^2 - \sigma_{RelCount}^2)^{1/2} \quad (5)$$

Here, as the total relative precision $\sigma_{RelTotal}$ of the X-ray intensity, an arbitrary sample is used for each kind of sample, and relative precision of the X-ray intensity experimentally obtained by repeatedly performing measurement, for example, about 50 times for each measurement line in a state where the mechanical elements of the X-ray fluorescence spectrometer are driven or replaced according to analysis conditions including a provisional counting time, can be used. In addition, as the counting relative precision $\sigma_{RelCount}$, relative precision of the X-ray intensity experimentally obtained by similarly repeatedly performing measurement for each measurement line in a state where no mechanical element of the X-ray fluorescence spectrometer is driven or replaced, can be used. Instead, the counting relative precision $\sigma_{RelCount}$ obtained by calculating the counting precision $\sigma_{Count}$ from a given counting loss correction coefficient τ, a given corrected intensity $I_C$, and a provisional counting time T or a specified counting time T, for example, based on equation (10) described later, and dividing the counting precision $\sigma_{Count}$ by the corrected intensity $I_C$, may be used.

As for the counting loss correction, various correction equations are known, and for example, the following equation (6) based on an extended dead time model can be used.

$$I_C = I_0 \times \exp(\tau I_C) \quad (6)$$

$I_C$: corrected intensity
$I_0$: uncorrected intensity (measured intensity itself before the counting loss correction is performed)
τ: counting loss correction coefficient (dead time)

In equation (6), since the corrected intensity $I_C$ is included on both sides, the corrected intensity $I_C$ is obtained by repeatedly performing calculation by the Newton method, based on the uncorrected intensity $I_0$ as measured and the given counting loss correction coefficient τ, until the corrected intensity $I_C$ for which the uncorrected intensity $I_0$ is the initial value converges.

Since the corrected intensity $I_C$ is larger than the uncorrected intensity $I_0$, the counting precision $\sigma_{Count}$ which is precision of the corrected intensity has a larger value than precision $\sigma_0$ of the uncorrected intensity and is worse as precision. As can be understood from the previous equation (6), the corrected intensity $I_C$ is a value obtained by multiplying the uncorrected intensity $I_0$ by a coefficient corresponding to this intensity $I_C$, and thus the counting precision $\sigma_{Count}$ can be obtained from the precision $\sigma_0$ of the uncorrected intensity. Based on this idea, in the calculation by the counting time calculation unit 13, as in the following equation (7), the counting precision $\sigma_{Count}$ is regarded as a product of the precision $\sigma_0$ of the uncorrected intensity and a gradient $\partial I_C/\partial I_0$ of the corrected intensity with respect to the uncorrected intensity.

$$\sigma_{Count} = \sigma_0 (\partial I_C/\partial I_0) \quad (7)$$

Here, the precision $\sigma_0$ of the uncorrected intensity is expressed as the following equation (8) from the previous equations (1) and (6) when the uncorrected intensity $I_0$ is assumed to follow statistical fluctuation, for example.

$$\sigma_0 = (I_0/T)^{1/2} = (I_C/(T \times \exp(\tau I_C)))_{1/2} \quad (8)$$

Moreover, the gradient $\partial I_C/\partial I_0$ of the corrected intensity with respect to the uncorrected intensity is expressed as the following equation (9) by partially differentiating the previous equation (6) with the uncorrected intensity $I_0$.

$$\partial I_C/\partial I_0 = \exp(\tau I_C)/(1-\tau I_C) \quad (9)$$

From these equations (7), (8), and (9), the following equation (10) is obtained.

$$\sigma_{Count} = ((\exp(\tau I_C))^{1/2}/(1-\tau I_C)) \times (I_C/T)^{1/2} \quad (10)$$

From this equation (10) and the previous equation (3), the following equations (11) and (12) are obtained.

$$T = I_C'/(\sigma_{Total}^2 - (\sigma_{RelInst} \times I_C)^2) \quad (11)$$

$$I_C' = I_C \times \exp(\tau I_C)/(1-\tau I_C)^2 \quad (12)$$

For each measurement line, the counting time calculation unit 13 calculates the counting time T from the specified total precision $\sigma_{Total}$ of the X-ray intensity, the given counting loss correction coefficient $\tau$, and the given corrected intensity $I_C$, based on the equations (11) and (12). Here, as for the total precision $\sigma_{Total}$ of the X-ray intensity, a desired value is specified by an operator using an input unit such as a keyboard or a touch panel which are not shown. The counting loss correction coefficient $\tau$ is obtained in advance by a known technique and is stored in the counting time calculation unit 13.

As for the corrected intensity $I_C$, a standard sample that is of the same kind as an unknown sample to be analyzed and whose composition is known is measured at a provisional counting time, and the corrected intensity $I_C$ obtained as described in the description of the previous equation (6) is used. In addition, when a current value of the X-ray tube is adjusted as an analysis condition related to the magnitude of the corrected intensity $I_C$, if the corrected intensity $I_C$ with which the total relative precision $\sigma_{RelTotal}$ of the X-ray intensity is minimized is desired to be confirmed, the corrected intensity $I_C$ assumed by the operator is input from the input unit. That is, the given corrected intensity $I_C$ includes both the corrected intensity $I_C$ given from another portion of the control unit 11 to the counting time calculation unit 13 as a calculated value based on the measured intensity and the corrected intensity $I_C$ specified directly by the operator via the input unit and given to the counting time calculation unit 13. As for the hardware reproducibility relative precision $\sigma_{RelInst}$, a value calculated based on the previous equation (5) from the total precision $\sigma_{Total}$ of the X-ray intensity and the counting relative precision $\sigma_{RelCount}$ which are obtained as described in the description of the previous equation (5), is used.

As described above, in the X-ray fluorescence spectrometer of the first embodiment, by regarding the counting precision $\sigma_{Count}$ as the product of the precision $\sigma_0$ of the uncorrected intensity and the gradient $\partial I_C/\partial I_0$ of the corrected intensity with respect to the uncorrected intensity, the effect of counting loss is appropriately reflected in the counting precision $\sigma_{Count}$. Thus, even when counting loss occurs, the counting time T can be calculated correctly from the specified total precision $\sigma_{Total}$ of the X-ray intensity. Therefore, for example, if the total precision $\sigma_{Total}$ of the X-ray intensity corresponding to desired analysis precision (precision of an analytical value that is a content and/or thickness) is specified and the calculated counting time T is confirmed and is excessively long, it is possible to measure an unknown sample with an appropriate counting time and appropriate analysis precision by increasing the total precision $\sigma_{Total}$ of the X-ray intensity in the permissible range and specifying again the total precision $\sigma_{Total}$.

Figure 2:
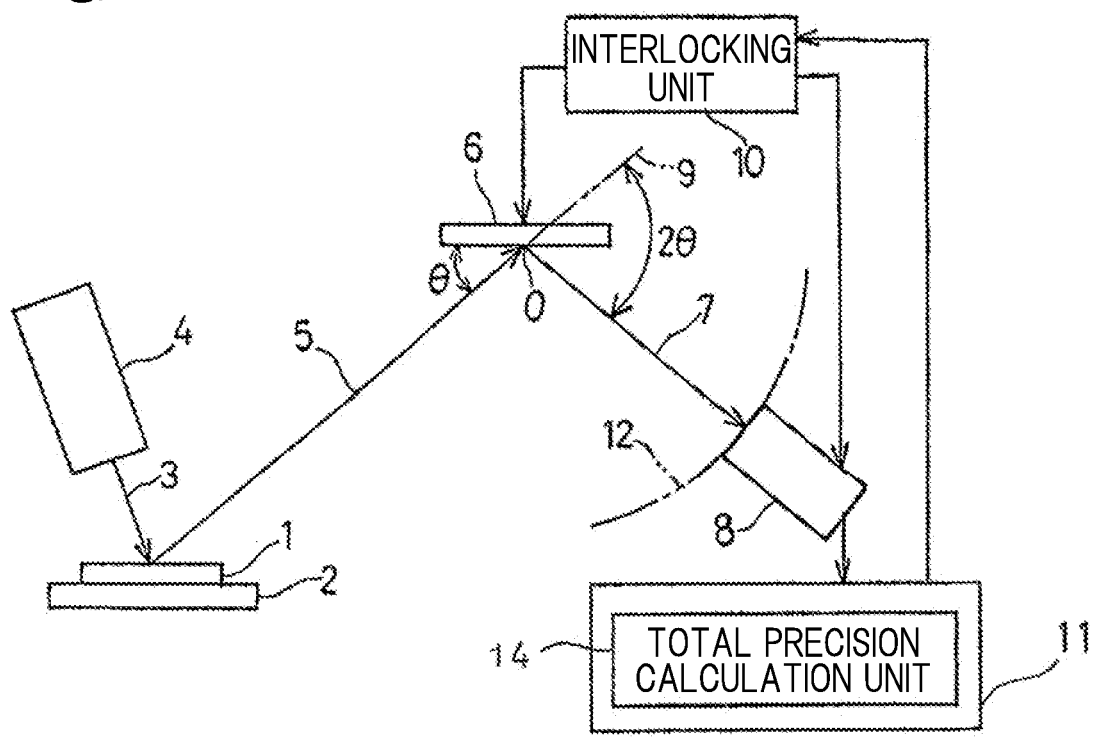
FIG. 2 is a schematic diagram showing an X-ray fluorescence spectrometer of a second embodiment of the present invention.

Next, an X-ray fluorescence spectrometer of a second embodiment of the present invention will be described. As shown in FIG. 2, the X-ray fluorescence spectrometer of the second embodiment is different from the X-ray fluorescence spectrometer of the first embodiment shown in FIG. 1, only in that instead of the counting time calculation unit 13, a total precision calculation unit 14 which calculates the total precision $\sigma_{Total}$ of the X-ray intensity for each measurement line 5 is provided as the program incorporated in the control unit 11. Thus, only the total precision calculation unit 14 will be described.

In the calculation by the total precision calculation unit 14 as well, as in the previous equation (3), the square of the total precision $\sigma_{Total}$ of the X-ray intensity is regarded as the sum of the square of the counting precision $\sigma_{Count}$ due to statistical fluctuation and counting loss and the square of the hardware reproducibility precision $\sigma_{Inst}$ due to the hardware reproducibility of the X-ray fluorescence spectrometer. In addition, as in the previous equation (7), the counting precision $\sigma_{Count}$ is regarded as the product of the precision $\sigma_0$ of the uncorrected intensity and the gradient $\partial I_C/\partial I_0$ of the corrected intensity with respect to the uncorrected intensity.

As for the total precision $\sigma_{Total}$ of the X-ray intensity, the following equation (13) and the previous equation (12) are obtained from the previous equation (10) and the previous equation (3).

$$\sigma_{Total} = (I_C'/T + (\sigma_{RelInst} \times I_C)^2)^{1/2} \quad (13)$$

$$I_C' = I_C \times \exp(\tau I_C)/(1-\tau I_C) \quad (12)$$

For each measurement line, the total precision calculation unit 14 calculates the total precision $\sigma_{Total}$ of the X-ray intensity from the specified counting time T, the given counting loss correction coefficient T, and the given corrected intensity $I_C$, based on the equations (13) and (12).

Here, as for the counting time T, a desired value is specified by the operator using the input unit such as a keyboard or a touch panel which are not shown. As for the counting loss correction coefficient $\tau$, the corrected intensity $I_C$, and the hardware reproducibility relative precision $\sigma_{RelInst}$, the same values as those used in the counting time calculation unit 13 are used.

In the X-ray fluorescence spectrometer of the second embodiment as well, by regarding the counting precision $\sigma_{Count}$ as the product of the precision $\sigma_0$ of the uncorrected intensity and the gradient $\partial I_C/\partial I_0$ of the corrected intensity with respect to the uncorrected intensity, the effect of counting loss is appropriately reflected in the counting precision $\sigma_{Count}$. Thus, even when counting loss occurs, the total precision $\sigma_{Total}$ of the X-ray intensity can be calculated correctly from the specified counting time T. Therefore, for example, if a desired counting time T is specified and the calculated total precision $\sigma_{Total}$ of the X-ray intensity or the analysis precision corresponding thereto is confirmed and is excessively large, it is possible to measure an unknown sample with an appropriate counting time and appropriate analysis precision by increasing and specifying again the counting time T.

Figure 3:
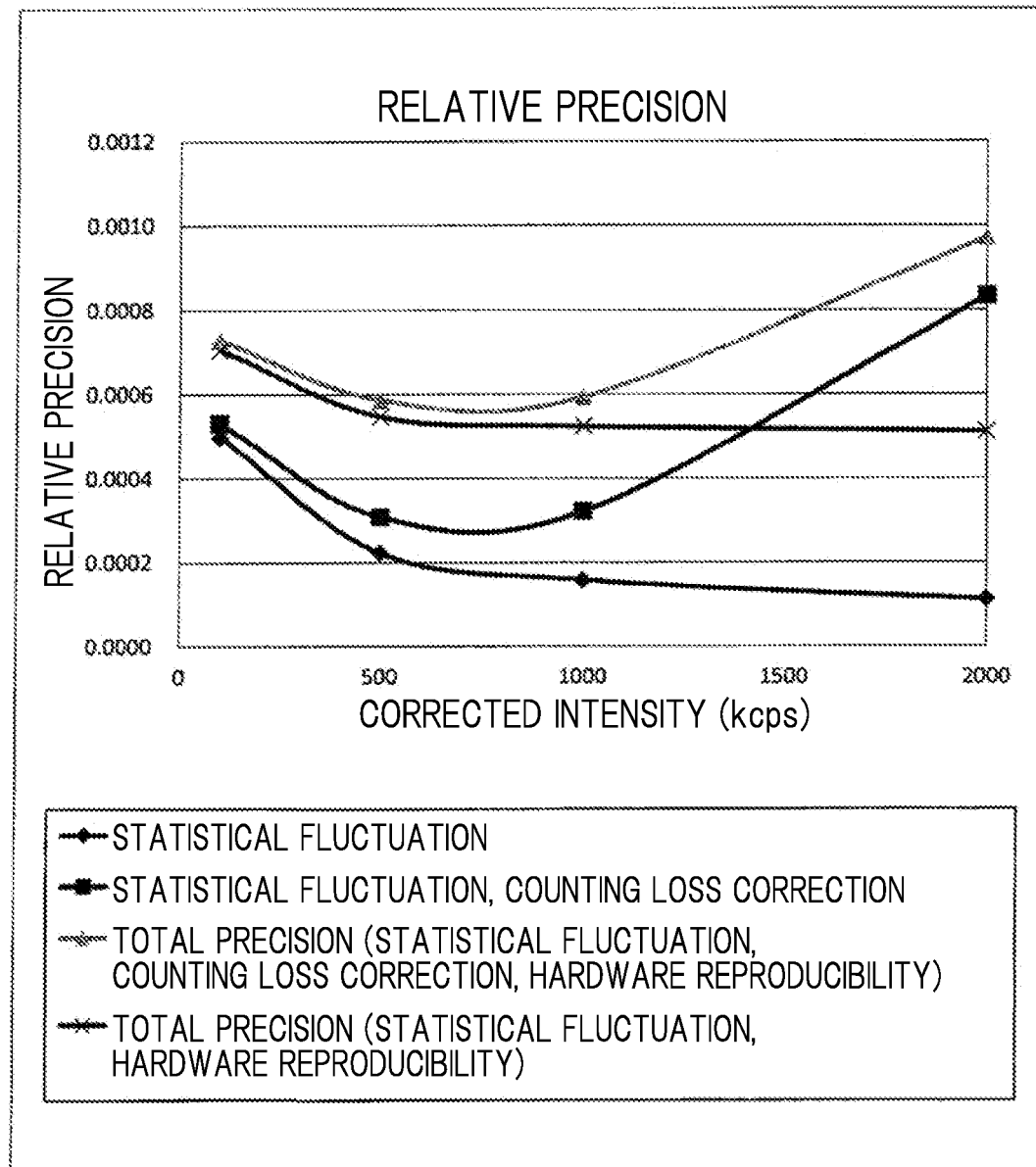
FIG. 3 is a diagram showing the relationship between relative precision and corrected intensity by various precision calculation methods.

FIG. 3 shows the relationship between relative precision and corrected intensity by various precision calculation methods. In FIG. 3, what is described as "STATISTICAL FLUCTUATION" is the relationship between the counting relative precision and the corrected intensity when only the counting precision due to statistical fluctuation is considered. The corrected intensity is substantially equal to the true X-ray intensity incident on the detector in the normal measured intensity range where counting loss correction is performed correctly. What is described as "STATISTICAL FLUCTUATION, COUNTING LOSS CORRECTION" is the relationship between the counting relative precision and the corrected intensity when the counting precision due to statistical fluctuation and counting loss is considered. As will be described later, the precision calculation method when the hardware reproducibility precision can be ignored in the present invention corresponds to this case.

What is described as "TOTAL PRECISION (STATISTICAL FLUCTUATION, HARDWARE REPRODUCIBILITY)" is the relationship between the total relative precision and the corrected intensity when the counting precision due to only statistical fluctuation and the hardware reproducibility precision are considered. The precision calculation method of the background art exemplified by citing Patent Document 2 corresponds to this case. What is described as "TOTAL PRECISION (STATISTICAL FLUCTUATION, COUNTING LOSS CORRECTION, HARDWARE REPRODUCIBILITY)" is the relationship between the total relative precision and the corrected intensity when the counting precision due to statistical fluctuation and counting loss and the hardware reproducibility precision are considered. The precision calculation methods in the first and second embodiments of the present invention correspond to this case. In the above precision calculation, when the hardware reproducibility precision is included, the value of the hardware reproducibility relative precision is set to 0.0005.

The relative precision of "STATISTICAL FLUCTUATION" is ideally high (small numerical value) precision that is not affected by counting loss and hardware reproducibility, but in actual measurement, the relative precision is always affected by hardware reproducibility, so that, like the relative precision of "TOTAL PRECISION (STATISTICAL FLUCTUATION, HARDWARE REPRODUCIBILITY)", the relative precision does not become less than the hardware reproducibility relative precision (here, 0.0005). In addition, apart from the effect of hardware reproducibility, in actual measurement, as the true X-ray intensity incident on the detector increases, counting loss occurs more frequently, and even if the corrected intensity is substantially equal to the true X-ray intensity, the deviation between the uncorrected intensity and the true X-ray intensity increases. Thus, like the relative precision of "STATISTICAL FLUCTUATION, COUNTING LOSS CORRECTION", the relative precision rises diagonally up to the right in a high intensity region.

In the present invention, the counting precision due to statistical fluctuation and counting loss is considered, and as described above, the counting precision is regarded as the product of the precision of the uncorrected intensity, which is the intensity before the counting loss correction is performed, and the gradient of the corrected intensity with respect to the uncorrected intensity. Accordingly, in the present invention, the effect of counting loss is appropriately reflected in the counting precision, and for example, like the relative precision of "TOTAL PRECISION (STATISTICAL FLUCTUATION, COUNTING LOSS CORRECTION, HARDWARE REPRODUCIBILITY)" in FIG. 3, the relative precision does not become less than the hardware reproducibility relative precision, rises diagonally up to the right in the high intensity region, and has a value that is in line with reality.

In the spectrometers of the first and second embodiments, the hardware reproducibility precision is taken into consideration for the total precision of the X-ray intensity, and the square of the total precision of the X-ray intensity is regarded as the sum of the square of the counting precision due to statistical fluctuation and counting loss and the square of the hardware reproducibility precision. However, when the hardware reproducibility precision can be ignored in the present invention, the total precision of the X-ray intensity may be regarded as the counting precision due to statistical fluctuation and counting loss. In this case, the following equations (14), (15), (16), and (17) are used instead of the previous equations (3), (4), (11), and (13), respectively.

$$\sigma_{Total} = \sigma_{Count} \quad (14)$$

$$\sigma_{RelTotal} = \sigma_{RelCount} \quad (15)$$

$$T = I_C'/\sigma_{Total}^2 \quad (16)$$

$$\sigma_{Total} = (I_C'/T)^{1/2} \quad (17)$$

Moreover, in the above description of the embodiments, the gross intensity obtained by measuring only the peak is used as the measured intensity, but the present invention can also be applied by a known technique to the case where the net intensity obtained by measuring the peak and its background(s) and performing background subtraction is used as the measured intensity.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . sample
3 . . . primary X-rays
5 . . . secondary X-rays (measurement line)
13 . . . counting time calculation unit
14 . . . total precision calculation unit

What is claimed is:

1. An X-ray fluorescence spectrometer which obtains a quantitative value of a content of a component in a sample and/or a quantitative value of a thickness of the sample, based on corrected intensities obtained by irradiating the sample with primary X-rays, measuring intensities of generated secondary X-rays, and performing counting loss correction, the X-ray fluorescence spectrometer comprising
a counting time calculation unit configured to calculate a counting time for each of measurement lines which are secondary X-rays to be measured for intensities, wherein
by regarding total precision of an X-ray intensity as counting precision due to statistical fluctuation and counting loss, and
by regarding the counting precision as a product of precision of an uncorrected intensity, which is an intensity before the counting loss correction is performed, and a gradient of the corrected intensity with respect to the uncorrected intensity,
the counting time calculation unit calculates the counting time from specified total precision of the X-ray intensity, a given counting loss correction coefficient, and a given corrected intensity for each measurement line.

2. An X-ray fluorescence spectrometer which obtains a quantitative value of a content of a component in a sample and/or a quantitative value of a thickness of the sample, based on corrected intensities obtained by irradiating the sample with primary X-rays, measuring intensities of generated secondary X-rays, and performing counting loss correction, the X-ray fluorescence spectrometer comprising a total precision calculation unit configured to calculate total precision of an X-ray intensity for each of measurement lines which are secondary X-rays to be measured for intensities, wherein by regarding the total precision of the X-ray intensity as counting precision due to statistical fluctuation and counting loss, and by regarding the counting precision as a product of precision of an uncorrected intensity, which is an intensity before the counting loss correction is performed, and a gradient of the corrected intensity with respect to the uncorrected intensity, the total precision calculation unit calculates the total precision of the X-ray intensity from a specified counting time, a given counting loss correction coefficient, and a given corrected intensity for each measurement line.

3. The X-ray fluorescence spectrometer as claimed in claim 1, wherein instead of regarding the total precision of the X-ray intensity as the counting precision due to statistical fluctuation and counting loss, the counting time calculation unit regards a square of the total precision of the X-ray intensity as a sum of a square of the counting precision due to statistical fluctuation and counting loss and a square of hardware reproducibility precision due to hardware reproducibility of the X-ray fluorescence spectrometer.

4. The X-ray fluorescence spectrometer as claimed in claim 2, wherein instead of regarding the total precision of the X-ray intensity as the counting precision due to statistical fluctuation and counting loss, the total precision calculation unit regards a square of the total precision of the X-ray intensity as a sum of a square of the counting precision due to statistical fluctuation and counting loss and a square of hardware reproducibility precision due to hardware reproducibility of the X-ray fluorescence spectrometer.

* * * * *